(12) United States Patent
Keener et al.

(10) Patent No.: US 7,172,861 B2
(45) Date of Patent: Feb. 6, 2007

(54) ACTIVITY-BASED ASSAY FOR RICIN-LIKE TOXINS

(75) Inventors: William K. Keener, Falling Waters, WV (US); Thomas E. Ward, Pennsylvania Furnace, PA (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 364 days.

(21) Appl. No.: 10/944,259

(22) Filed: Sep. 16, 2004

(65) Prior Publication Data

US 2006/0057596 A1 Mar. 16, 2006

(51) Int. Cl.
C12Q 1/00 (2006.01)
C12Q 1/68 (2006.01)
C07H 21/02 (2006.01)
C07H 21/04 (2006.01)

(52) U.S. Cl. .............................. 435/4; 435/6; 536/23.1; 536/24.3

(58) Field of Classification Search ............... 435/4, 435/6; 536/23.1, 24.3
See application file for complete search history.

(56) References Cited

U.S. PATENT DOCUMENTS

| | | | |
|---|---|---|---|
| 2003/0003454 A1* | 1/2003 | Livneh et al. .................. | 435/6 |
| 2004/0086918 A1* | 5/2004 | Loewy et al. .................. | 435/6 |
| 2005/0176035 A1* | 8/2005 | Crothers ........................ | 435/6 |
| 2006/0014154 A1* | 1/2006 | Eshoo ............................ | 435/6 |
| 2006/0134631 A1* | 6/2006 | Krokan et al. ................. | 435/6 |

OTHER PUBLICATIONS

Barbani et al., Barbieri et al., Som ribosome-inactivating proteins depurinate ribosomal RNA at multiple sites. Biochem. J. 286: 14 (1992).*
Barbieri et al., Polynucleotide:adenosine glycosidase activity of ribosome-inactivating proteins: effect on DNA, RNA and poly(A). Nucleic Acids Res. 25: 518-522 (1997).*
Boorstein et al., Definitive Identification of Mammalian 5-Hydroxymethyluracil DNA N-Glycosylase Activity as SMUG1. J. Biol. Chem. 276 (45) : 41991-41997 (2001).*
Brigotti et al. A rapid and sensitive method to measure the enzymatic activity of ribosome-inactivating proteins. Nucleic Acids Res. 26: 4306-4307 (1998).*
Kreklau et al., Nucleic Acids Res. 29: 2558-2566 (2001).*
Kumar et al.,Contrasting effects of single stranded DNA binding protein on the activity of uracil DNA glycosylase from *Escherichia coli* towards different DNA substrates. Nucleic Acids Res. 25: 2336-2343 (1997).*
Langer et al., A nonradioactive assay for ribosome-inactivating proteins. Anal. Biochem. 243: 150-153 (1997).*
Lawrence et al., "Toxicity profile of chloroacetaldehyde," J. Pharm. Sci 61: 19-25 (1972).*
Nicolas et al. A new class of DNA glycosylase/apurinic/apyrimidinic lysases that act on specific adenines in single-stranded DNA. J. Biol. Chem. 273: 17216-17220 (1998).*
Nicolas et al., Gelonin is an unusual DNA glycosylase that removes adenine from single-stranded DNA, normal base pairs and mismatches. J. Biol. Chem. 275: 31399-31406 (2000).*
Sheppard et al., A DNA enzyme withg N-glycosylase activity. PNAS 97 (14) : 7802-7807 (2000).*
Xia et al. DNA glycosylase activity assay based on streptavidin paramagnetic bead substrate capture. Anal. Biochem. 298 : 322-326 (2001).*
Zamboni et al., High-pressure-liquid chromatographic and fluorimetric methods for the determination of adenine released from ribosomes by ricin and gelonin. Biochem. J. 259: 639-643 (1989).*

* cited by examiner

*Primary Examiner*—Ethan Whisenant
(74) *Attorney, Agent, or Firm*—Wells St. John

(57) ABSTRACT

A method of detecting N-glycosylase activity in a sample involves incubating an oligodeoxyribonucleotide substrate containing a deoxyadenosine or deoxyuridine residue with the sample to be tested such that the N-glycosylase, if present, hydrolyzes the deoxyadenosine or deoxyuridine residue to result in an N-glycosylase product having an abasic site. A primer is annealed to the N-glycosylase product, and the primer is extended with a DNA polymerase, such as Taq DNA polymerase, that pauses at abasic sites. The resulting extension products are melted from the N-glycosylase product, allowed to form hairpins due to self-complementarity, and further extended in the presence of labeled precursors to result in labeled products. Extension products synthesized from undigested substrate as template do not result in labeled products. Thus, detection of labeled products results in detection of N-glycosylase activity. Oligodeoxyribonucleotide substrates, primer, and positive controls and a kit for N-glycosylase assay are also disclosed.

39 Claims, 4 Drawing Sheets

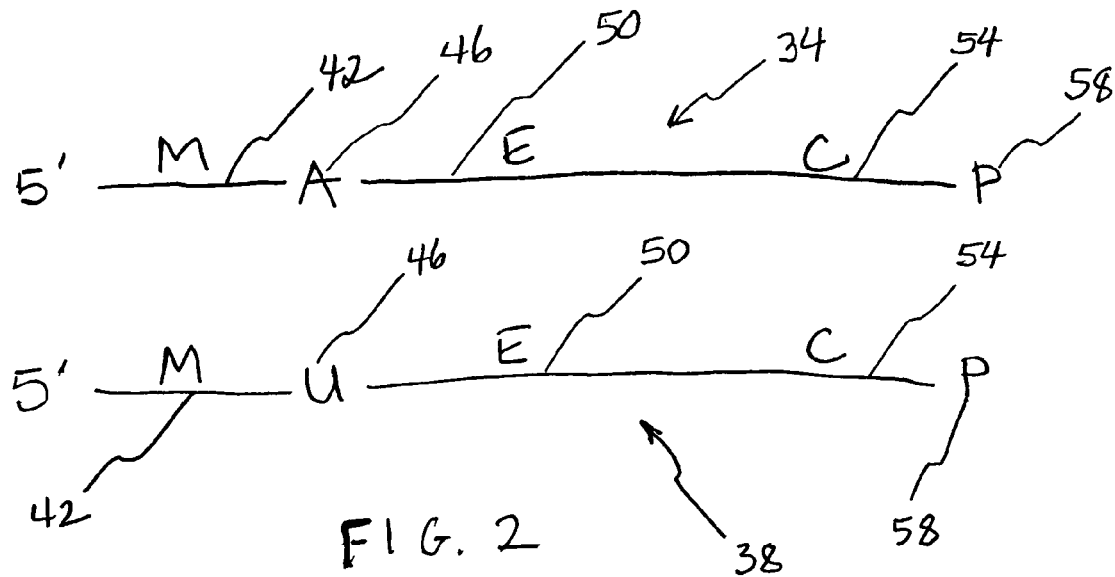
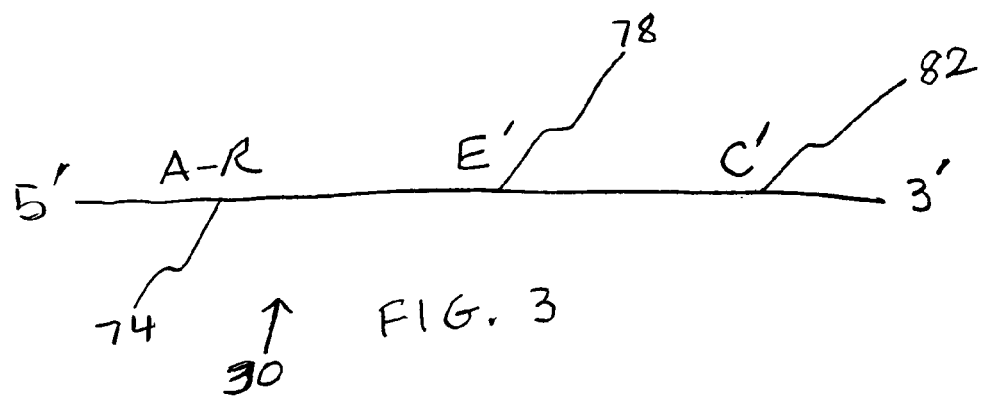

SEQUENCE LISTING

<160> NUMBER OF SEQ ID NOS: 9

<210> SEQ ID NO 1
<211> LENGTH: 44
<212> TYPE: DNA
<213> ORGANISM: Artificial sequence
<220> FEATURE:
<223> OTHER INFORMATION: Substrate for saporin, gelonin with one
      adenine.

<400> SEQUENCE: 1
ttttgtccag cttcggtgcc ggttctccct gtcgtgtcgt tggt           44

<210> SEQ ID NO 2
<211> LENGTH: 43
<212> TYPE: DNA
<213> ORGANISM: Artificial sequence
<220> FEATURE:
<223> OTHER INFORMATION: Substrate for uracil N-glycosylase.
<220> FEATURE:
<221> NAME/KEY: modified_base
<222> LOCATION: (7)..(7)
<223> OTHER INFORMATION: uracil

<400> SEQUENCE: 2
ttttgcttgc ttcggtgccg gttctccctg tcgtgtcgtt ggt            43

<210> SEQ ID NO 3
<211> LENGTH: 36
<212> TYPE: DNA
<213> ORGANISM: Artificial sequence
<220> FEATURE:

```
<223> OTHER INFORMATION: Positive control with artificial, stable abasic
      site based on tetrahydrofuran.

<400> SEQUENCE: 3
tgcttcggtg ccggttctcc ctgtcgtgtc gttggt                            36

<210> SEQ ID NO 4
<211> LENGTH: 35
<212> TYPE: DNA
<213> ORGANISM: Artificial sequence
<220> FEATURE:
<223> OTHER INFORMATION: Positive control mimicking truncated product
      due to abiotic hydrolysis at toxin-generated abasic site at 94
      degrees C.

<400> SEQUENCE: 4
gcttcggtgc cggttctccc tgtcgtgtcg ttggt                             35

<210> SEQ ID NO 5
<211> LENGTH: 50
<212> TYPE: DNA
<213> ORGANISM: Artificial sequence
<220> FEATURE:
<223> OTHER INFORMATION: Primer with A-rich 5' tail to promote
      incorporation of dUTP-fluorophores.

<400> SEQUENCE: 5
ttgcatatat tatattatca ggatgcttcg gtgccaacga cacgacaggg             50

<210> SEQ ID NO 6
<211> LENGTH: 17
<212> TYPE: DNA
<213> ORGANISM: Artificial sequence
<220> FEATURE:
<223> OTHER INFORMATION: 3' Segment of primer

<400> SEQUENCE: 6
ccaacgacac gacaggg                                                 17

<210> SEQ ID NO 7
<211> LENGTH: 17
<212> TYPE: DNA
<213> ORGANISM: Artificial sequence
<220> FEATURE:
<223> OTHER INFORMATION: C (complementary) segment of substrates and
      positive controls.

<400> SEQUENCE: 7
ccctgtcgtg tcgttgg                                                 17

<210> SEQ ID NO 8
<211> LENGTH: 17
<212> TYPE: DNA
<213> ORGANISM: Artificial sequence
<220> FEATURE:
<223> OTHER INFORMATION: E (extension) segment of substrates and
      positive controls.

<400> SEQUENCE: 8
gcttcggtgc cggttct                                                 17

<210> SEQ ID NO 9
<211> LENGTH: 19
<212> TYPE: DNA
<213> ORGANISM: Artificial sequence
```

```
-continued

<220> FEATURE:
<223> OTHER INFORMATION: Adenine-rich segment of primer.

<400> SEQUENCE: 9
atatattata ttatcagga                                                    19
```

US 7,172,861 B2

ACTIVITY-BASED ASSAY FOR RICIN-LIKE TOXINS

GOVERNMENT RIGHTS

This invention was made with government support under Contract No. DE-AC07-99ID13727 with the Department of Energy. The government has certain rights in the invention.

BACKGROUND OF THE INVENTION

This invention relates to methods and compositions for detecting N-glycosylase activity. More particularly, this invention relates to sensitive detection of N-glycosylase toxins based on their biological activity.

Ribosome-inactivating proteins (RIPs) include adenine-specific N-glycosylases, such as ricin, saporin, and gelonin, which depurinate ribosomal RNA to cause irreversible inhibition of protein synthesis. L. Barbieri et al., "Some ribosome-inactivating proteins depurinate ribosomal RNA at multiple sites," 286 Biochem. J. 1–4 (1992); M. Zamboni et al., "High-pressure-liquid chromatographic and fluorimetric methods for the determination of adenine released from ribosomes by ricin and gelonin," 259 Biochem. J. 639–643 (1989). Alternatively referred to as (adenosine) N-glycosidases when acting on RNA, these enzymes also remove adenine from DNA molecules, including single-stranded or denatured DNA. E. Nicolas et al., "Gelonin is an unusual DNA glycosylase that removes adenine from single-stranded DNA, normal base pairs and mismatches," 275 J. Biol. Chem. 31399–31406 (2000); L. Barbieri et al., "Polynucleotide:adenosine glycosidase activity of ribosome-inactivating proteins: effect on DNA, RNA and poly(A)," 25 Nucleic Acids Res. 518–522 (1997). Likewise, uracil DNA glycosylase (UDG) can remove uracil from deoxyuridine residues in oligodeoxyribonucleotides (ODNs). N. V. Kumar & U. Varshney, "Contrasting effects of single stranded DNA binding protein on the activity of uracil DNA glycosylase from *Escherichia coli* towards different DNA substrates," 25 Nucleic Acids Res. 2336–2343 (1997). The resulting abasic sites have intact phosphodiester backbones when purified N-glycosylases are used, L. Barbieri et al., "Polynucleotide: Adenosine glycosidase is the sole activity of ribosome-inactivating proteins on DNA," 128 J. Biochem. (Tokyo) 883–889 (2000), although backbone cleavage (lyase activity) has been reported. E. Nicolas et al., "A new class of DNA glycosylase/apurinic/apyrimidinic lysases that act on specific adenines in single-stranded DNA," 273 J. Biol. Chem. 17216–17220 (1998).

N-Glycosylases, when naturally coupled to cell-binding lectins, are also known as potential bioterrorism agents because of their toxic properties. These toxins remove adenine residues from ribosomal RNA, thereby inactivating ribosomes and inhibiting protein synthesis, which are required for viability of cells. Ricin and abrin are two biothreats that contain N-glycosylases.

Activity-based assays previously reported for N-glycosylases involve radiolabeled DNA substrates, M. Brigotti et al., "A rapid and sensitive method to measure the enzymatic activity of ribosome-inactivating proteins," 26 Nucleic Acids Res. 4306–4307 (1998); L. Xia & T. R. O'Connor, "DNA glycosylase activity assay based on streptavidin paramagnetic bead substrate capture," 298 Anal. Biochem. 322–326 (2001), or the derivatization of released adenine to a fluorescent product using chloroacetaldehyde, which is highly toxic. M. Zamboni et al., supra; W. H. Lawrence et al., "Toxicity profile of chloroacetaldehyde," 61 J. Pharm. Sci 19–25 (1972). In both cases, separation of unreacted DNA substrate was required. The classic approach for assaying RIPs uses inhibition of in vitro translation as a measure of RIP activity. Typically, the complex, unstable reagents necessary for this approach are derived from lysates of rabbit reticulocytes. M. Langer et al., "A nonradioactive assay for ribosome-inactivating proteins," 243 Anal. Biochem. 150–153 (1997). Since ribosomal inactivation produces a signal that is inversely proportional to the amount of RIP present, inhibitory substances other than RIPs may cause false responses. A fluorescence-based assay has been reported, which directly measures N-glycosylase activity on short ODN substrates having defined sites for enzyme action, but this method is not conducive to signal amplification and thus is limited in sensitivity. E. L. Kreklau et al., "A novel fluorometric oligonucleotide assay to measure O(6)-methylguanine DNA methyltransferase, methylpurine DNA glycosylase, 8-oxoguanine DNA glycosylase and abasic endonuclease activities: DNA repair status in human breast carcinoma cells overexpressing methylpurine DNA glycosylase," 29 Nucleic Acids Res. 2558–2566 (2001).

Thus, while prior N-glycosylase assays are known and are generally suitable for their limited purposes, they possess certain inherent deficiencies that detract from their overall utility in field-testing for bioterrorism agents.

In view of the foregoing, it will be appreciated that providing a potentially field-deployable assay for detecting N-glycosylase activity would be a significant advancement in the art.

BRIEF SUMMARY OF THE INVENTION

It is a feature of the present invention to provide an assay for N-glycosylase activity that is simple, compatible with current detection platforms, robust, highly sensitive, readily adaptable to real-time analysis, and complementary to antibody-based assays, and involves nonhazardous and stable reagents.

Another feature of the present invention is to provide an assay for N-glycosylase activity that exhibits very low background signal in the absence of toxin.

Still another feature of the invention is the potential for differentiation of closely related toxins according to their different activities.

These and other features can be addressed by providing a method for detecting N-glycosylase activity comprising:

(a) providing an oligodeoxyribonucleotide (ODN) substrate comprising (1) a 5' segment, (2) a deoxyadenosine residue comprising an adenine residue covalently bonded to a 2-deoxyribose residue through a β-linkage, or a deoxyuridine residue comprising a uracil residue covalently bonded to a 2-deoxyribose residue through a β-linkage, and (3) a 3' segment, which lies 3' to the deoxyadenosine or deoxyuridine residue, mixing the ODN substrate with a sample to be tested for N-glycosylase activity to form a mixture, and incubating the mixture such that the N-glycosylase activity, if present, hydrolyzes the β-linkage, thereby releasing the adenine or uracil residue and producing an N-glycosylase ODN product comprising an abasic site at the hydrolyzed adenosine or deoxyuridine residue;

(b) inactivating the N-glycosylase activity in the mixture;

(c) treating the N-glycosylase product and any unreacted substrate that may be present in the mixture with an oligodeoxyribonucleotide primer under conditions such that a limited extension product of the primer is synthesized and, if the substrate is present in the mixture, a longer extension product of the primer is synthesized, wherein the primer is selected to be sufficiently complementary to the 3' segment of the N-glycosylase product and the substrate to hybridize therewith such that the limited extension product has a first 3' terminus corresponding to a residue immediately 3' to the abasic site of the N-glycosylase product and the longer extension product has a second 3' terminus corresponding to the 5' terminus of the substrate, and wherein the primer further comprises a 5' segment thereof that does not hybridize with the N-glycosylase product or the substrate, wherein the limited extension product is sufficiently self-complementary to form a hairpin structure such that the first 3' terminus is base paired such that it can be further extended using the 5' segment as a template, and wherein the longer extension product is sufficiently self-complementary to form a hairpin structure, but the second 3' terminus is not base paired and is not extended using the 5' segment as a template;

(d) separating the limited and longer extension products from the N-glycosylase product and the substrate, respectively, on which they were synthesized to produce corresponding single-stranded molecules;

(e) treating the single-stranded molecules generated from step (d) under conditions such that additional limited and longer primer extension products are synthesized using the N-glycosylase product and any substrate that may be present as templates, and the limited primer extension products form hairpin structures that are further extended, using the 5' segment as template, such that a label is incorporated to result in a labeled product, but the longer primer extension products do not substantially incorporate the label; and (f) separating and detecting the labeled product, thereby detecting N-glycosylase activity.

Steps (d) and (e) are repeated at least once and ordinarily are repeated multiple times. Step (d) is typically accomplished by denaturing the limited and longer extension products from their templates, and such denaturing may be caused by heating the double-stranded extension products to a temperature that melts them apart. Steps (c) and (e) are typically accomplished using an enzyme, such as DNA polymerase, more particularly, a thermostable DNA polymerase. The DNA polymerase is one that pauses while attempting to incorporate nucleotides in primer extension products corresponding to abasic template sites, such as Taq DNA polymerase. In an illustrative embodiment of the invention, inactivation of the N-glycosylase activity is carried out using heat.

In another illustrative embodiment of the invention, the substrate is represented by SEQ ID NO:1 or SEQ ID NO:2, and the primer is represented by SEQ ID NO:5. In still another illustrative embodiment of the invention, steps (b), (c), (d), and (e) are carried out simultaneously above room temperature during thermocycling using an enzyme that, after being exposed to a temperature of about 50°95° C., forms the limited and longer extension products and the labeled product during steps (c) and (e). Illustratively, the label can be a fluorescent label, and detecting the labeled product comprises fluorescence detection. A still further illustrative embodiment of the invention comprises carrying out steps (c) through (f) with a positive control oligodeoxyribonucleotide substituted for the substrate and comparing results obtained therefrom with results obtained from carrying out steps (a) through (f) with the substrate. The positive control oligodeoxyribonucleotide can be a member selected from the group consisting of SEQ ID NO:3, SEQ ID NO:4, and mixtures thereof.

Another illustrative embodiment of the invention comprises a method for detecting N-glycosylase activity comprising:

(a) providing an oligodeoxyribonucleotide substrate for N-glycosylase activity, wherein the substrate has a structure represented by 5'-MAEC-P-3' or 5'-MUEC-P-3', wherein M is a mis-match directing segment, E is an extension template segment, C is a complementary segment, A is a deoxyadenosine residue comprising adenine linked to a 2-deoxyribose residue by a β-linkage, U is a deoxyuridine residue comprising uracil linked to a 2-deoxyribose residue by a β-linkage, and P is a phosphate group, mixing the substrate with a sample to be tested for N-glycosylase activity to form a mixture, and incubating the mixture such that the N-glycosylase activity, if present, hydrolyzes the β-linkage, thereby releasing the adenine or uracil residue and producing an N-glycosylase product that has a structure represented by 5'-MXEC-P-3', wherein X is an abasic site at the hydrolyzed A or U;

(b) inactivating the N-glycosylase activity in the mixture to form an N-glycosylase-inactivated mixture;

(c) treating the N-glycosylase product and any substrate that may be present in the N-glycosylase-inactivated mixture with an oligodeoxyribonucleotide primer under conditions such that limited and longer extension products of the primer are synthesized, wherein the primer is selected to be sufficiently complementary to C of 5'-MAEC-P-3', 5'-MUEC-P-3', and 5'-MXEC-P-3' to hybridize therewith such that the limited extension product that is hybridized to 5'-MXEC-P-3' has a first 3' terminus corresponding to a residue immediately 3' to X of 5'-MXEC-P-3' and the longer extension product has a second 3' terminus corresponding to the 5' terminus of 5'-MAEC-P-3' or 5'-MUEC-P-3', and wherein the primer further comprises a 5' segment thereof that does not hybridize with the N-glycosylase product or the substrate, wherein the limited extension product is sufficiently self-complementary to form a hairpin structure such that the first 3' terminus is base paired such that it can be further extended using the 5' segment as a template, and wherein the longer extension product is sufficiently self-complementary to form a hairpin structure, but the second 3' terminus is not base paired and is not extended using the 5' segment as a template;

(d) separating the limited and longer extension products from the N-glycosylase product and the substrate on which they were synthesized to produce corresponding single-stranded molecules;

(e) treating the single-stranded molecules generated from (d) under conditions such that additional limited and longer primer extension products are synthesized using the N-glycosylase product and any substrate that may be present as templates, and the limited primer extension products form hairpin structures that are further extended, using the 5' segment as template, such that a label is incorporated to result in a labeled product; and (f) separating and detecting the labeled product, thereby detecting N-glycosylase activity.

Yet another illustrative embodiment of the invention comprises a method for detecting N-glycosylase activity comprising:

(a) providing an oligodeoxyribonucleotide substrate comprising (1) a 5' segment, (2) a deoxyadenosine residue comprising an adenine residue covalently bonded to a 2-deoxyribose residue through a β-linkage, or a deoxyuridine residue comprising a uracil residue covalently bonded to a 2-deoxyribose residue through a β-linkage, and (3) a 3' portion, which lies 3' to the deoxyadenosine or deoxyuridine residue, wherein the substrate is SEQ ID NO: 1, SEQ ID NO:2, a mixture thereof, mixing the substrate with a sample to be tested for N-glycosylase activity to form a mixture, and incubating the mixture such that the N-glycosylase activity, if present, hydrolyzes the β-linkage, thereby releasing the adenine or uracil residue and producing an N-glycosylase product comprising an abasic site at the hydrolyzed deoxyadenosine or deoxyuridine residue and a 3' portion;

(b) inactivating the N-glycosylase activity in the mixture;

(c) treating the N-glycosylase product and any substrate that may be present in the mixture with an oligodeoxyribonucleotide primer under conditions such that a limited extension product of the primer is synthesized and, if the substrate is present in the mixture, a longer extension product of the primer is synthesized, wherein the primer is selected to be sufficiently complementary to the 3' portion of the N-glycosylase product and the substrate to hybridize therewith such that the limited extension product has a first 3' terminus corresponding to a residue immediately 3' to the abasic site of the N-glycosylase product and the longer extension product has a second 3' terminus corresponding to the 5' terminus of the substrate, and wherein the primer further comprises a 5' portion thereof that does not hybridize with the N-glycosylase product or the substrate, wherein the primer is SEQ ID NO:5, wherein the limited extension product is sufficiently self-complementary to form a hairpin structure such that the first 3' terminus is base paired such that it can be further extended using the 5' portion as a template, and wherein the longer extension product is sufficiently self-complementary to form a hairpin structure, but the second 3' terminus is not base paired and cannot be extended using the 5' segment as a template;

(d) separating the limited and longer extension products from the N-glycosylase product and the substrate on which they were synthesized to produce corresponding single-stranded molecules;

(e) treating the single-stranded molecules generated from step (d) under conditions such that additional limited and longer primer extension products are synthesized using the N-glycosylase product and any substrate that may be present as templates, and the limited primer extension products form hairpin structures and are further extended, using the 5' portion as template, such that a label is incorporated to result in a labeled product; and (f) separating and detecting the labeled product, thereby detecting N-glycosylase activity.

Still further illustrative embodiments of the invention comprises oligonucleotides represented by SEQ ID NO:1 and SEQ ID NO:2 as substrates for an N-glycosylase assay, oligonucleotides represented by SEQ ID NO:3 and SEQ ID NO:4 as positive controls for an N-glycosylase assay, and an oligonucleotide represented by SEQ ID NO:5 as a primer for an N-glycosylase assay according to the present invention.

Another illustrative embodiment of the invention comprises a kit for detecting N-glycosylase activity comprising an N-glycosylase substrate oligodeoxyribonucleotide, wherein the substrate oligodeoxyribonucleotide is SEQ ID NO:1, SEQ ID NO:2, or mixtures thereof; a positive control oligodeoxyribonucleotide, wherein the positive control oligodeoxyribonucleotide is SEQ ID NO:3, SEQ ID NO:4 or mixtures thereof; a primer oligodeoxyribonucleotide, wherein the primer oligodeoxyribonucleotide is SEQ ID NO:5; and a container in which the substrate, positive control, and primer oligodeoxyribonucleotides are disposed.

BRIEF DESCRIPTION OF THE SEVERAL VIEWS OF THE DRAWINGS

FIG. 2 shows a schematic representation of illustrative substrate oligonucleotides of N-glycosylase activity according to the present invention.

FIG. 3 shows a schematic representation of an illustrative primer for use in detecting N-glycosylase activity according to the present invention.

DETAILED DESCRIPTION

Figure 1:
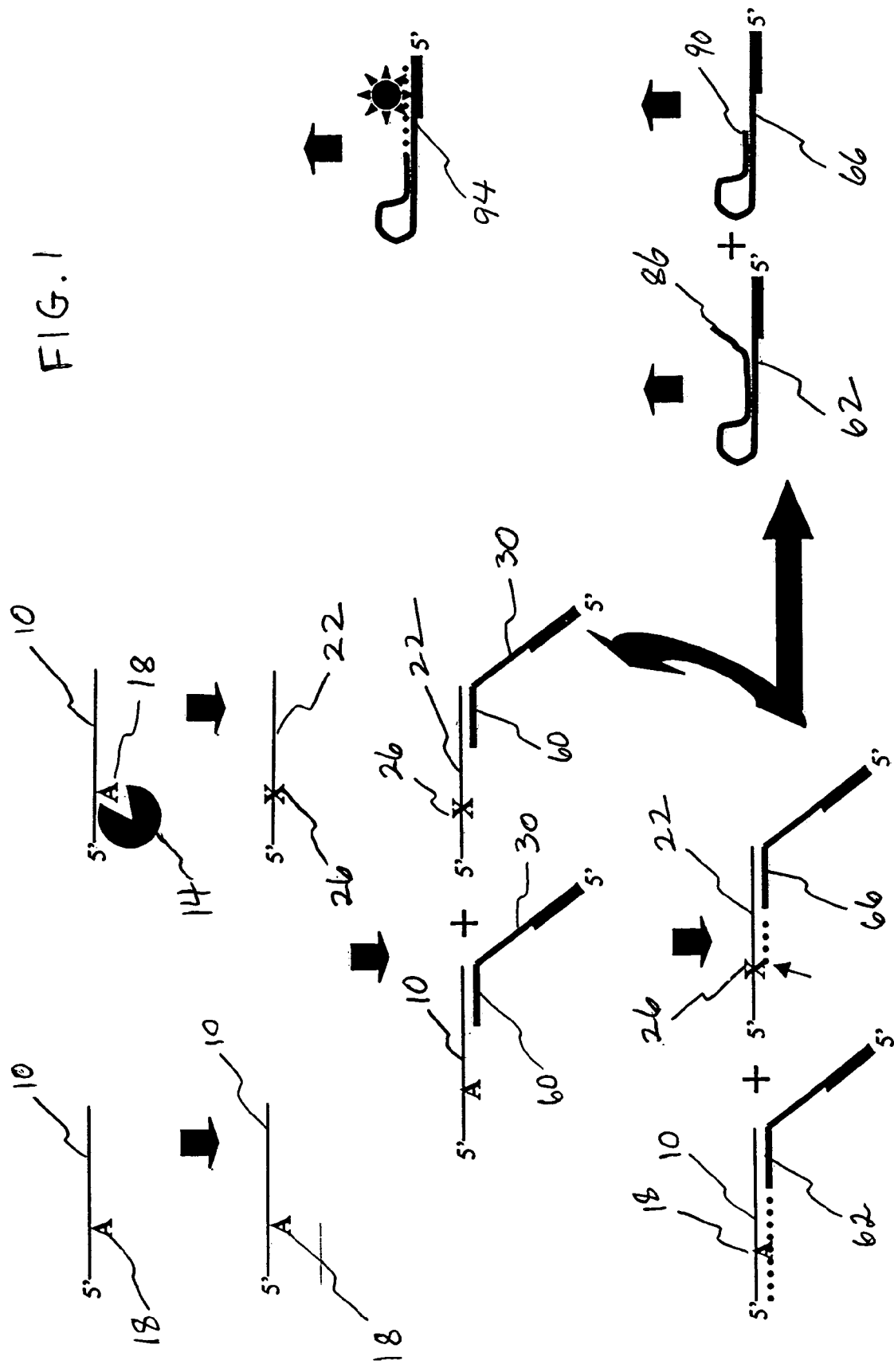
FIG. 1 shows a schematic representation of a two-stage signal amplification mechanism for detecting N-glycosylase activity.

Before the present activity-based assay for N-glycosylases, such as ricin-like toxins, and compositions for use in such assay are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to a method using "a substrate" includes reference to two or more of such substrates, reference to "an extension product" include reference to two or more of such extension products, and reference to "the primer" includes reference to two or more of such primers.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "abasic site" means a site in an oligonucleotide chain where a base (adenine, cytosine, guanine, thymine, or uracil) has been removed from a nucleotide residue, leaving the corresponding deoxyribose or ribose residue.

As used herein, "N-glycosylase activity" means the enzyme-catalyzed hydrolysis of the bond between a base and a deoxyribose or ribose residue in a nucleotide residue of an oligonucleotide chain. An abasic site is created by N-glycosylase activity.

As mentioned above, currently known methods for assaying N-glycosylase activity suffer from several disadvantages for detecting bioterrorism agents in the field. The present invention solves these problems. For example, the present invention uses fluorescence detection instead of radioisotopes, thus reducing the hazards associated with radioactive reagents. Further, the present invention is carried out in one reaction tube, thus minimizing the number of steps required and simplifying the assay. The present invention also uses a signal amplification step, which leads to high sensitivity while producing very low background. Still further, the present invention is based on thermocycling, a currently used detection platform, and uses only one enzyme, Taq polymerase or equivalent, which is well known and readily available. The assay uses nonhazardous, stable reagents. Moreover, the present invention is readily adaptable to real-time analysis, can be used with current strategies for concentrating and purifying toxins from samples, and is complementary to antibody-based assays, which are currently in use. The present invention can also be used for differentiating closely related toxins according to the slightly different activities of such related toxins.

Taq DNA polymerase is a thermostable DNA polymerase that possesses a 5' to 3' polymerase activity and a double-strand specific 5' to 3' exonuclease activity. Taq DNA polymerase was originally detected in *Thermus aquaticus*, but the gene for Taq DNA polymerase has been cloned, and the commercially available enzyme is purified from *Escherichia coli*. Taq DNA polymerase has been used extensively in primer extension applications, such as the polymerase chain reaction (PCR). Moreover, Taq DNA polymerase has been found to pause at abasic sites. P. H. Patel et al., A single highly mutable catalytic site amino acid is critical for DNA polymerase fidelity, 276 J. Biol. Chem. 5044–5051 (2001). This behavior of pausing at abasic sites is used in the present invention to discriminate between unreacted substrate oligonucleotides and products formed by the activity of toxins. This discrimination leads to amplification of the signal by Taq DNA polymerase only when toxin activity was present in the first of two phases of the assay. The nonhazardous reagents are specially designed to enable this discrimination.

The N-glycosylase activity assay of the present invention comprises a two-level cascade, resulting in an amplified signal when N-glycosylase activity is present. The first level of the cascade comprises an N-glycosylase (toxin) reaction, wherein a substrate oligonucleotide having a defined site for toxin action is mixed with a test sample. If N-glycosylase activity is present in the test sample, then the substrate oligonucleotide is digested to result in a modified oligonucleotide comprising an abasic site. One molecule of toxin can convert many molecules of substrate to N-glycosylase product. Of course, if no N-glycosylase activity is present in the test sample, then the substrate oligonucleotide remains intact. The second level of the cascade comprises a signal-amplifying reaction. The substrate oligonucleotide is subjected to thermocycling in the presence of Taq DNA polymerase and the four deoxyribonucleoside triphosphates, one of which is labeled with a fluorescent tag. If the substrate oligonucleotide was modified by N-glycosylase activity to contain an abasic site, then the fluorescent tag is incorporated into a previously extended primer oligonucleotide during further extension. If the substrate oligonucleotide has no abasic site, then further primer extension is thwarted and the fluorescent tag is not incorporated into the primer. Therefore, detection of the label in an extended primer indicates the presence of N-glycosylase activity in the sample.

This N-glycosylase activity assay will now be described in more detail with reference to FIGS. 1–3. Referring first to FIG. 1, a substrate oligonucleotide 10 is selected according to the N-glycosylase 14 that is to be assayed. The substrate oligonucleotide 10 contains a target site 18 for the selected N-glycosylase 14 activity to be assayed. In one illustrative embodiment of the invention, the substrate oligonucleotide 10 contains a deoxyadenosine (A) residue, which is digested to result in a product oligonucleotide 22 having an abasic site 26, if adenine-specific N-glycosylase activity is present in the test sample. In another illustrative embodiment of the invention, the substrate oligonucleotide contains a deoxyuridine residue, which is digested to result in a product having an abasic site 26, if uracil-specific N-glycosylase activity is present in the test sample.

Referring now to FIG. 2, illustrative substrate oligonucleotides 34, 38 according to the present invention comprise segments that function cooperatively with the primer 30 (FIGS. 1 and 3) for use in detecting the presence of N-glycosylase activity in a sample. Beginning at the 5'-end of the substrate oligonucleotide and moving to the 3'-end thereof, there are a mis-match directing segment (M) 42, a target site (A or U) 46, an extension template segment (E) 50, a complementary segment (C) 54, and a phosphate group (P) 58. The complementary segment (C) 54 is configured for being sufficiently complementary to the 3' portion of the primer 30 such that they can hybridize to form a partial duplex 60 (FIG. 1). The extension template segment (E) 50 functions as a template for extension of the primer 30 in a primer extension reaction. The sequence of the extension template segment (E) 50, or a portion thereof, is also present in the primer, as will be described below, such that the extended primer is self-complementary and will self-hybridize to form a hairpin structure after melting of the extended primer from the product oligonucleotide or from the substrate oligonucleotide, as will be described in more detail below. The target site 46 is either an A or a U residue, and is a target for the N-glycosylase reaction. If N-glycosylase activity hydrolyzes the A or U residue, then the target site 46 becomes an abasic site. The mis-match directing segment (M) 42 functions as a template for primer extension when the primer hybridizes to the substrate oligonucleotide 10. However, the mis-match directing segment (M) 42 does not function as a template for primer extension when the primer hybridizes to the product oligonucleotide 22 because the extended primer terminates opposite the residue to the immediate 3' side of the abasic site. The portion of the extended primer that is complementary to the mis-match directing segment (M) 42 is not complementary to any other sequence of the primer and, thus does not hybridize to any other sequence of the primer.

FIG. 3 shows a schematic representation of a primer 30 according to the present invention. The 5' portion of the primer 30 is a deoxyadenosine-rich (A-R) sequence 74. When this A-R sequence 74 functions as a template for primer extension, the incorporation of labeled dUTP residues is permitted opposite each of these deoxyadenosine residues of the primer. The sequence of the primer 30 3' to the A-R sequence 74 is the same as a portion of the E segment 50 of the substrate oligonucleotide 34, 38. This sequence of the primer 30 is referred to as the E' sequence 78. When the primer 30 is extended, with the E segment 50 functioning as the template for such extension, the resulting extension is complementary to the E' sequence 78, thus resulting in self-complementarity of the extended primer. Under conditions suitable for hybridization, these self-complementary segments hybridize to each other, resulting in a hairpin structure of the extended primer. At the 3' end of the primer 30 is a sequence (C' sequence 82) complementary to the C segment 54 of the substrate oligonucleotide 34, 38. Under conditions suitable for hybridization, the substrate oligonucleotide and the product oligonucleotide hybridize to the primer 30 because of the complementarity of the C segment 54 and the C' sequence of the primer 30.

Referring again to FIG. 1, after the N-glycosylase reaction is completed, primer 30 is added to the reaction tube, along with DNA polymerase and dNTPs. The primer is annealed to the product nucleotide 22 and any substrate oligonucleotide 10 that remains. Polymerase-catalyzed extension of the primer 30 results in a full length extension product 62 from the unreacted substrate oligonucleotide 10 template and a truncated extension product 66 from the N-glycosylase product oligonucleotide 22 template. These extension products are then melted from their corresponding templates.

After the full length extension product 62 and the truncated extension product 66 are melted from the corresponding substrate oligonucleotide 10 or N-glycosylase product oligonucleotide 22 and then are returned to conditions suitable for hybridization of complementary sequences, the full length extension product 62 and the truncated extension product 66 can self-hybridize to form hairpin structures. Since the 3' end 86 of the full length extension product 62 is not complementary, and thus does not hybridize, to any portion of the full length extension product 62, the truncated extension product 66, the substrate oligonucleotide 10, or the product oligonucleotide 22, it is not extended further upon being placed in conditions that would otherwise be suitable for primer extension. The 3' end 90 of the truncated extension product 66, on the other hand, is complementary, and thus hybridizes, to the E' sequence 78 of the truncated extension product 66. Thus, when the truncated extension product 66 has self-hybridized and is placed in conditions suitable for primer extension, the truncated extension product 66 is further extended, and the adenine-rich (A-R) segment 74 of the truncated extension product 66 functions as the template for such primer extension. In the presence of labeled dUTP, such labeled dUTP residues are incorporated into the resulting extension product, which is referred to herein as labeled extension product 94. This labeled extension product 94 can be detected, and the detection of such labeled extension product 94 indicates the presence of N-glycosylase activity in the original sample.

Now that the reaction steps of the assay have been described, the assay will be described again to further illustrate how the assay can be carried out in practical terms. A sample to be assayed is mixed with a substrate oligonucleotide, and the resulting mixture is incubated at 30° C. for 10 minutes to allow any N-glycosylase present in the sample to digest the substrate oligonucleotide to result in product oligonucleotide containing an abasic site. The mixture is then heated to 94° C. for two minutes to inactivate the N-glycosylase present in the mixture. Next, primer oligonucleotide, a thermostable DNA polymerase (e.g., Taq polymerase), the four deoxyribonucleotides, labeled dUTP, and the necessary salts, buffers, and the like are added to the reaction tube. Thermocycling is then commenced. For example, cycles of 30 seconds at 50° C., 15 seconds at 72° C., and 15 seconds at 94° C. could be repeated a selected number of times. During the first 50° C. (annealing) cycle, the primer anneals to the substrate and product oligonucleotides present in the reaction mixture. During the 72° C. (extension) cycle, the primer is extended by a thermostable DNA polymerase-catalyzed primer extension reaction. Copies of the primer that annealed to substrate oligonucleotide are extended to full length. Copies of the primer that annealed to N-glycosylase product oligonucleotide are extended as far as the abasic site, resulting in the truncated extension product. During the 94° C. (melting) cycle, the full length extension product and the truncated extension product are melted from their corresponding substrates. During the second and subsequent annealing cycles, the substrate and product oligonucleotides can anneal to previously unreacted primers, and the full length and truncated extension products can self-hybridize to form hairpin structures. During the second and subsequent extension cycles, the hairpin structures derived from truncated extension products will be further extended, resulting in the incorporation of the labeled dUTP into the resulting labeled extension product, while the full length extension product will not be further extended because of a mismatched 3' end. At the completion of the selected number of cycles, the contents of the reaction tube are tested for detection of labeled extension products, and the presence of labeled extension products indicates the presence of N-glycosylase activity in the original sample, while the absence of labeled extension products indicates the absence of N-glycosylase activity in the sample.

Detection of the labeled extension product can be by any technique known in the art. For example, the contents of the reaction tube can be subjected to gel electrophoresis followed by fluorescence detection, in the case of a fluorescent or fluorogenic label.

An illustrative example of the N-glycosylase (toxin) reaction, or the first level of the cascade according to the present invention, can be carried out in a reaction tube, such as a tube that would be suitable for PCR, in a total volume of 5 µl at 30° C. The reaction mixture contains the test sample, 2.5 pmol of the substrate oligonucleotide, and a suitable buffer, such as AKT buffer, which has a final concentration of 7 mM sodium acetate, 100 mM KCl, and 0.1% v/v Triton X-100, pH 4.0. It has been determined that the Triton X-100 enhances the detection of very small quantities of toxin, presumably by keeping the toxin solubilized and preventing adsorption to the walls of the tube. In addition to AKT buffer, the toxin reactions contain the toxin sample. Also, the substrate or control oligonucleotide can be added in the amount of 2.5 pmol per reaction. Working stocks of oligonucleotides (5 pmol/µl) can be obtained by diluting primary stocks (200 pmol/µl) with AKT buffer.

A typical amplification reagent mixture comprises (per 1,000 µl): 850 µl of nuclease-free water, 100 µl of 10X Taq buffer (15 mM $MgCl_2$, 500 mM KCl, 1% Triton X-100, 100 mM Tris-HCl, pH 9.0; Promega Cat. No. M1881), 20 µl dNTP mix (see below), 20 µl Taq DNA polymerase (5 units/µl; Promega Cat. No. M2665), and 10 µl primer (SEQ ID NO:5; 100 pmol/µl). The dNTP mix comprises (per 100

μl): 65 μl Tris-EDTA buffer (pH 8.0), 10 μl of 1 mM ChromaTide Alexa Fluor 488-5-dUTP (dUTP-fluor; Molecular Probes, Eugene, Oreg.; Cat. No. C-11397), 10 μl of 1 mM dTTP, and 5 μl each of dATP, dGTP, and dCTP (100 mM stocks). Hence, the concentrations in the dNTP mix are 0.1 mM dUTP-fluor and dTTP, and 5 mM each of dATP, dGTP, and dCTP. After addition of the amplification reagent mixture, the contents of each tube are mixed by pipette, and the tubes are returned to the thermocycler. The tubes are then processed through a selected number of thermocycles of melting, annealing, and extension. Illustratively, thirty-five thermocycles may be used, wherein melting is carried out at 94° C. for 15 sec, annealing is carried out at 50° C. for 30 sec, and extension is carried out at 72° C. for 15 sec. In this example, the total time required for thermocycling would be about 1 hour 20 minutes.

EXAMPLE 1

ODNs were obtained from Integrated DNA Technologies (IDT; Coralville, Iowa). To restrict the site of action of the N-glycosylases to one site on each ODN substrate molecule, substrates contained a single adenine (A; SEQ ID NO:1) or uracil (U; SEQ ID NO:2-ttttgcutgcttcggtgccggttctc-cctgtcgtgtcgttggt) base amid ODN segments having specific functions in the Taq-catalyzed reactions. Positive control ODNs simulated depurinated substrates (ccggcttgcFtgcttcg-gtgccggttctccctgtcgtgtcgttggt-P, wherein F is a tetrahydrofuran-based spacer, and P is a phosphate group; SEQ ID NO:3) or substrates hydrolyzed following depurination (SEQ ID NO:4). Abasic sites hydrolyze abiotically at elevated temperature and pH. M. E. Fárez-Vidal et al., Characterization of uracil-DNA glycosylase activity from *Trypanosoma cruzi* and its stimulation by AP endonuclease, 29 Nucleic Acids Res. 1549–1555 (2001). A primer (SEQ ID NO:5) was designed so that its 3' segment (SEQ ID NO:6) would anneal to the complementary segment (C; SEQ ID NO:7). Extension of the primer across an E segment (SEQ ID NO:8), but stopping at the abasic site created by N-glycosylase activity, leads to a primer-derived hairpin with its 3' end matched in the stem, and thus competent for further extension along the adenine-rich 5' segment of the primer (SEQ ID NO:9) that causes incorporation of the fluorescent label into the stem (FIG. 1). Without backbone hydrolysis and/or depurination to the immediate 5' side of an E segment (SEQ ID NO:8), extension of the primer across a mismatch-directing segment (M), followed by melting and then self-annealing of the extended primer, lead to a primer-derived hairpin with a mismatched 3' end, which is not readily extended. The slight background signal observed with unreacted substrate ODNs (e.g., FIG. 4, lane 5) may be explained by the limited ability of Taq to extend mismatched 3' termini. M. M. Huang et al., Extension of base mispairs by Taq DNA polymerase: implications for single nucleotide discrimination in PCR, 20 Nucleic Acids Res. 4567–4573 (1992).

The pausing behavior of Taq at abasic sites in the template strand allows the assay to function as shown in FIG. 1. P. H. Patel et al., A single highly mutable catalytic site amino acid is critical for DNA polymerase fidelity, 276 J. Biol. Chem. 5044–5051 (2001). The ability of Taq to insert a fluorescent nucleotide analogue across from dAMP residues enables fluorescent labeling during extension of the primer-derived hairpin stem (Chromatide® Alexa Fluor® 488-5-dUTP, herein referred to as dUTP-fluor; Molecular Probes, Eugene, Oreg.).

N-glycosylase reactions (total volume, 5 μl; 30° C.) were performed with commercial enzyme preparations of saporin-SO6 (Advanced Targeting Systems, San Diego, Calif.; also known as saporin-S6), L. Barbieri et al., "Polynucleotide:adenosine glycosidase activity of ribosome-inactivating proteins: effect on DNA, RNA and poly(A)," 25 Nucleic Acids Res. 518–522 (1997), uracil N-glycosylase (Epicentre, Madison, Wis.), and gelonin (Sigma, St. Louis, Mo.). For the adenine N-glycosylases, the reaction buffer included 7 mM sodium acetate, 100 mM potassium chloride, and 0.1% v/v Triton® X-100 (pH 4.0; AKT buffer) (L. Barbieri et al., Polynucleotide:adenosine glycosidase activity of ribosome-inactivating proteins: effect on DNA, RNA and poly(A), 25 Nucleic Acids Res. 518–522 (1997)). Typically, reactions were initiated when 1 μl of an appropriate dilution of glycosylase in AKT buffer delivered the desired amount of glycosylase to 4 μl of AKT buffer containing 2.5 pmol of ODN substrate. UDG reactions occurred in TE buffer (10 mM Tris, 1 mM EDTA, pH 8.0) without Triton® X-100. After incubations of specific durations at 30° C., the temperature was increased and remained at 94° C. for 2 min to inactivate the glycosylase. Afterward, the temperature was lowered to 25° C. for addition of the amplification reagents (50 μl per tube). The amplification reagent mixture comprised (per 1,000 μl): 850 μl nuclease-free water (Promega, Madison, Wis.), 100 μl 10X Taq buffer (15 mM MgCl2, 500 mM KCl, 1% Triton® X-100, 100 mM Tris-HCl, pH 9.0; Promega), 20 μl dNTP mix, 20 μl Taq (5 units/μl; Promega), and 10 μl primer (100 pmol/μl in TE buffer). The dNTP mix comprised (per 100 μl): 65 μl TE buffer, 10 of 1 mM dUTP-fluor, 10 μl of 1 mM dTTP, and 5 μl each of dATP, dGTP, and dCTP (100 mM each; New England Biolabs, Beverly, Mass.). Thermocycling involved melting, annealing, and extension temperatures of 94° C. (15 sec), 50° C. (30 sec), and 72° C. (15 sec), respectively. After 35 cycles, 25 μl aliquots of each reaction were combined with loading dye (5 μl; Promega), and analyzed by gel electrophoresis (4% NuSieve® GTG® agarose; Cambrex Corp., East Rutherford, N.J.; 100 V, 0.5 h). Densitometric scanning of gel images provided quantitative results (FIGS. 4 & 5A&B).

Figure 4:
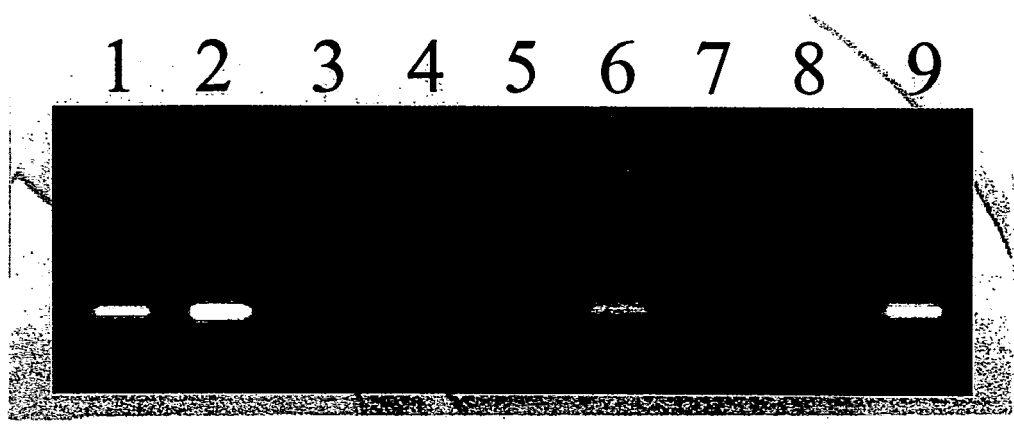
FIG. 4 shows gel analysis of Taq-generated, fluorescent amplification products derived from reactions catalyzed by two N-glycosylases, saporin and uracil N-glycosylase, with various controls.
Figure 5A:
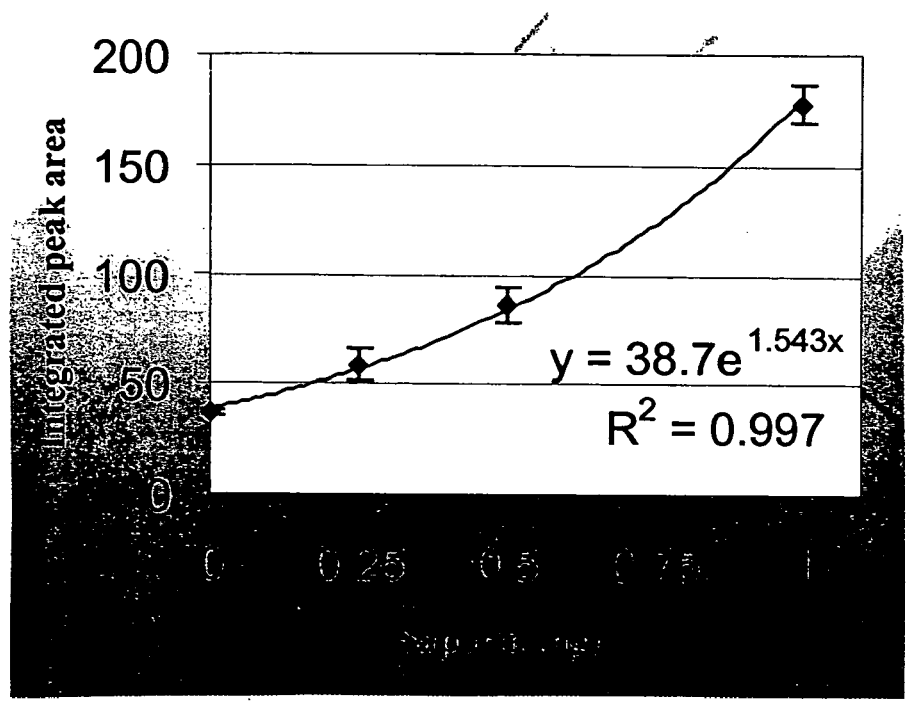
FIGS. 5A&B show the effects of varying the amount of saporin or its incubation time with substrates on fluorescent amplification products measured by gel analysis.

FIG. 4 shows gel analysis of Taq-generated, fluorescent amplification products derived from reactions catalyzed by two N-glycosylases, saporin and uracil N-glycosylase, with various controls. One set of triplicate samples is shown. Densitometric scanning of gel bands with an AlphaImager 2200 (Alpha Innotech Corp., San Leandro, Calif.) quantified the intensity of each band; averages and standard deviations are shown in parentheses. Oligodeoxyribonucleotide substrates (ODNs; 2.5 pmol per reaction) are abbreviated: M, mismatch-directing template segment; E, extension-directing template segment; C, complementary segment that anneals to primer; P, 3' phosphate group; F, tetrahydrofuran-based stable abasic site; A, (deoxy)adenosine residue; U, (deoxy)uridine residue. Gel lanes: 1, MFEC-P with no N-glycosylase (552.0±32.4); 2, EC-P with no N-glycosylase (594.0±40.8); 3, saporin (1 ng) with no ODN substrate (no bands detected); 4, saporin (1 ng) inactivated by heat (94° C., 2 min), then combined with MAEC-P (42.7±17.2); 5, MAEC-P with no saporin (26.7±2.5); 6, saporin (1 ng) with MAEC-P (399.0±65.9); 7, saporin (1 ng) with MUEC-P (26.0±1.7); 8, uracil N-glycosylase (17 pg) plus MAEC-P (8.3±0.6); 9, uracil N-glycosylase (17 pg) plus MUEC-P (590.3±30.0).

The slight background signal observed in the absence of glycosylase (FIG. 4, lane 5) was presumably due in part to incorporation of some dUTP-fluor into extended primer opposite the single dAMP in the unreacted ODN substrate, MAEC-P. To minimize this background, dTTP was included at an equimolar concentration with the dUTP-fluor (0.1 mM). This concentration of dTTP did not prevent incorporation of dUTP-fluor opposite one or more of the eight dAMP residues in the 5' segment of the primer. This diagnostic incorporation of dUTP-fluor in the hairpin stem was suppressed by increasing the dTTP concentration 2.5-fold. Therefore, equimolar concentrations of dTTP and dUTP-fluor—with incorporation of dTTP clearly favored by Taq—served to minimize the background signal while limiting suppression of the signal dependent on glycosylase activity. With equimolar dTTP and dUTP-fluor, preliminary data indicated that gelonin (1 ng) activity was also detectable using MAEC-P.

The limit of detection for saporin was below 100 pg (3.3 fmol) per reaction. After 60-min incubations with 100 pg saporin (30° C.), gel analysis yielded a signal that was 5.9±2.1 times greater than the signal obtained without saporin (±standard deviation; n=3). Methods dependent on radioactivity or chloroacetaldehyde are several-fold less sensitive. M. Brigotti et al., supra; L. Barbieri et al., "Polynucleotide:adenosine glycosidase activity of saporin-L1: effect on DNA, RNA and poly(A)," 319 Biochem. J. 507–513 (1996); L. Barbieri et al., 25 Nucleic Acids Res. 518–522 (1997). Though the present method is less sensitive than those based on ribosome inactivation, such methods are not specific for RIPs. M. Brigotti et al., supra. In contrast, ODN substrates can be used to differentiate glycosylases with varying activities (FIG. 2). E. L. Kreklau et al., supra.

Also, any sample generating signals with both MAEC-P and MUEC-P, albeit unlikely, would indicate nonspecific nuclease activity.

Figure 5B:
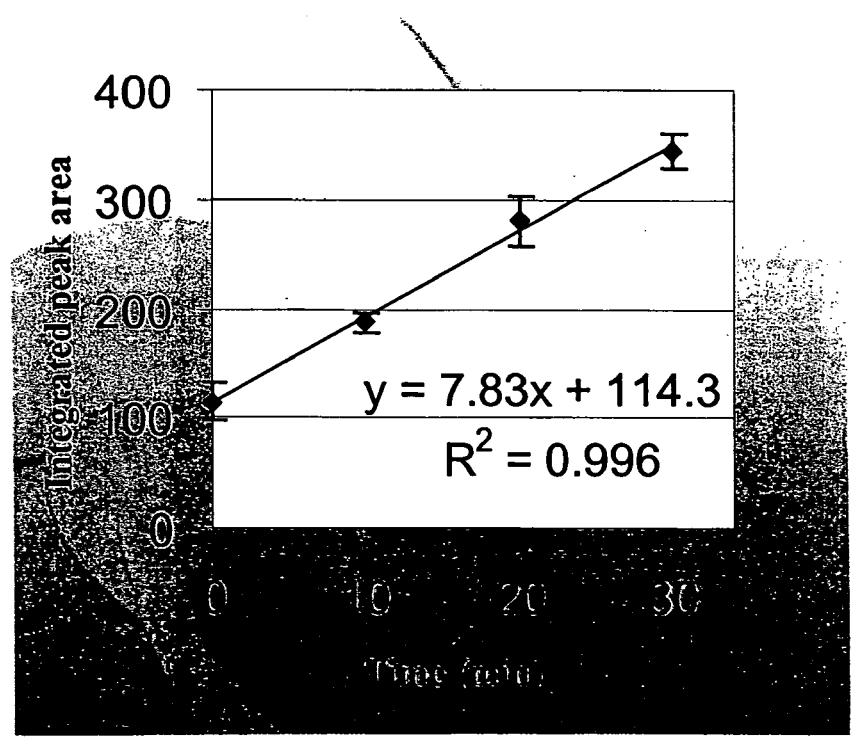

FIGS. 5A&B show the effects of varying the amount of saporin or its incubation time with substrates on fluorescent amplification products measured by gel analysis. Densitometric scanning of gel bands provided band intensity values. Averaged band intensity values are shown with standard deviation error bars (n=4; n=3 for points on y axes where x=0). Data points are not directly comparable between graphs as data were obtained from different experiments. FIG. 5A shows the effects of varying the amount of saporin on 10-min reactions at 30° C. FIG. 5B shows a time course using 0.5 ng saporin per reaction (linear regression analysis, $R^2$=0.996). The x axis indicates the number of minutes reactions were incubated at 30° C. before the temperature was increased over 40 sec to 94° C. and held there for 2 min, inactivating the saporin.

FIGS. 5A&B show that the signal produced by this assay increases as the amount of saporin increases, at least within the range of amounts of toxin tested. The concave-up curve in FIG. 5A can be explained by a loss of activity due to adsorption of toxin to the sides of the tubs, which is proportionally greater at lower toxin concentrations. FIG. 5B reveals a linear increase in signal with time of glycosylase treatment. In this case, any loss of toxin on tube walls should be constant since the amount of toxin was not varied. As expected with the use of a single primer, the linear nature of the amplification, with respect to the number of thermocycles, was demonstrated with MFEC-P.

What is claimed is:

1. A method for detecting N-glycosylase activity comprising:
   (a) providing an oligodeoxyribonucleotide substrate comprising (1) a 5' segment, (2) a deoxyadenosine residue comprising an adenine residue covalently bonded to a 2-deoxyribose residue through a β-linkage, or a deoxyuridine residue comprising a uracil residue covalently bonded to a 2-deoxyribose residue through a β-linkage, and (3) a 3' segment, which lies 3' to the deoxyadenosine or deoxyuridine residue,
   mixing the substrate with a sample to be tested for N-glycosylase activity to form a mixture, and
   incubating the mixture such that the N-glycosylase activity, if present, hydrolyzes the β-linkage, thereby releasing the adenine or uracil residue and producing an N-glycosylase product comprising an abasic site at the hydrolyzed deoxyadenosine or deoxyuridine residue;
   (b) inactivating the N-glycosylase activity in the mixture to result in an N-glycosylase-inactivated mixture;
   (c) treating the N-glycosylase product and any substrate that may be present in the N-glycosylase-inactivated mixture with an oligodeoxyribonucleotide primer under conditions such that a limited extension product of the primer is synthesized and, if the substrate is present in the mixture, a longer extension product of the primer is synthesized,
      wherein the primer is selected to be sufficiently complementary to the 3' portion of the N-glycosylase product and the substrate to hybridize therewith such that the limited extension product has a first 3' terminus corresponding to a residue to the immediate 3' side of the abasic site of the N-glycosylase product and the longer extension product has a second 3' terminus corresponding to the 5' terminus of the substrate, and wherein the primer further comprises a 5' segment thereof that does not hybridize with the N-glycosylase product or the substrate,
      wherein the limited extension product is sufficiently self-complementary to form a hairpin structure such that the first 3' terminus is base paired such that it can be further extended using the 5' segment as a template, and
      wherein the longer extension product is sufficiently self-complementary to form a hairpin structure, but the second 3' terminus is not base paired and is not extended using the 5' segment as a template;
   (d) separating the limited and longer extension products from the N-glycosylase product and the substrate, respectively, on which they were synthesized to produce corresponding single-stranded molecules;
   (e) treating the single-stranded molecules generated from step (d) under conditions such that additional limited and longer primer extension products are synthesized using the N-glycosylase product and any substrate that may be present as templates, and the limited primer extension products form hairpin structures and are further extended, using the 5' portion as template, such that a label is incorporated to result in a labeled product, but the longer primer extension products do not substantially incorporate the label; and
   (f) separating and detecting the labeled product, thereby detecting N-glycosylase activity.

2. The method of claim 1 wherein steps (d) and (e) are repeated at least once.

3. The method of claim 1 wherein step (d) is accomplished by denaturing.

4. The method of claim 3 wherein the denaturing is caused by heating.

5. The method of claim 1 wherein steps (c) and (e) are accomplished using an enzyme.

6. The method of claim 5 wherein the enzyme is a DNA polymerase.

7. The method of claim 6 wherein the DNA polymerase pauses while attempting to incorporate nucleotides in primer extension products corresponding to abasic template sites.

8. The method of claim 7 wherein the DNA polymerase is Taq DNA polymerase.

9. The method of claim 1 wherein the inactivating the N-glycosylase activity is carried out using heat.

10. The method of claim 1 wherein the substrate is represented by SEQ ID NO:1 or SEQ ID NO:2, and the primer is represented by SEQ ID NO:5.

11. The method of claim 1 wherein steps (b), (c), (d), and (e) are carried out simultaneously above room temperature during thermocycling using an enzyme that, after being exposed to a temperature of about 50°–95° C., forms the limited and longer extension products and the labeled product during steps (c) and (e).

12. The method of claim 1 wherein the label is a fluorescent label.

13. The method of claim 12 wherein detecting the labeled product comprises fluorescence detection.

14. The method of claim 1 further comprising carrying out steps (c) through (f) with a positive control oligodeoxyribonucleotide substituted for the substrate and comparing results obtained therefrom with results obtained from carrying out steps (a) through (f) with the substrate.

15. The method of claim 14 wherein the positive control oligodeoxyribonucleotide is a member selected from the group consisting of SEQ ID NO:3, SEQ ID NO:4, and mixtures thereof.

16. A method for detecting N-glycosylase activity comprising:
   (a) providing an oligodeoxyribonucleotide substrate for N-glycosylase activity, wherein the substrate has a structure represented by 5'-MAEC-P-3' or 5'-MUEC-P-3', wherein M is a mis-match directing segment, E is an extension template segment, C is a complementary segment, A is a deoxyadenosine residue comprising adenine linked to a 2-deoxyribose residue by a β-linkage, U is a deoxyuridine residue comprising uracil linked to a 2-deoxyribose residue by a β-linkage, and P is a phosphate group, mixing the substrate with a sample to be tested for N-glycosylase activity to form a mixture, and incubating the mixture such that the N-glycosylase activity, if present, hydrolyzes the β-linkage, thereby releasing the adenine or uracil residue and producing an N-glycosylase product that has a structure represented by 5'-MXEC-P-3', wherein X is an abasic site at the hydrolyzed A or U;

(b) inactivating the N-glycosylase activity in the mixture;

(c) treating the N-glycosylase product and any substrate that may be present in the mixture with an oligodeoxyribonucleotide primer under conditions such that limited and longer extension products of the primer are synthesized, wherein the primer is selected to be sufficiently complementary to C of 5'-MAEC-P-3', 5'-MUEC-P-3', and 5'-MXEC-P-3' to hybridize therewith such that the limited extension product has a first 3' terminus corresponding to a residue to the immediate 3' side of X of 5'-MXEC-P-3' and the longer extension product has a second 3' terminus corresponding to the 5' terminus of 5'-MAEC-P-3' or 5'-MUEC-P-3', and wherein the primer further comprises a 5' segment thereof that does not hybridize with the N-glycosylase product or the substrate, wherein the limited extension product is sufficiently self-complementary to form a hairpin structure such that the first 3' terminus is base paired such that it can be further extended using the 5' portion as a template, and wherein the longer extension product is sufficiently self-complementary to form a hairpin structure, but the second 3' terminus is not base paired and is not extended using the 5' portion as a template;

(d) separating the limited and longer extension products from the N-glycosylase product and the substrate, respectively, on which they were synthesized to produce corresponding single-stranded molecules;

(e) treating the single-stranded molecules generated from (d) under conditions such that additional limited and longer primer extension products are synthesized using the N-glycosylase product and any substrate that may be present as templates, and the limited primer extension products form hairpin structures and are further extended, using the 5' segment as template, such that a label is incorporated to result in a labeled product; and (f) separating and detecting the labeled product, thereby detecting N-glycosylase activity.

17. The method of claim 16 wherein steps (d) and (e) are repeated at least once.

18. The method of claim 16 wherein step (d) is accomplished by denaturing.

19. The method of claim 18 wherein the denaturing is caused by heating.

20. The method of claim 16 wherein step (c) and (e) are accomplished using an enzyme.

21. The method of claim 20 wherein the enzyme is a DNA polymerase.

22. The method of claim 21 wherein the DNA polymerase pauses while attempting to incorporate nucleotides in primer extension products corresponding to abasic template sites.

23. The method of claim 22 wherein the DNA polymerase is Taq DNA polymerase.

24. The method of claim 16 wherein the inactivating the N-glycosylase activity is carried out using heat.

25. The method of claim 16 wherein the substrate is SEQ ID NO:1 or SEQ ID NO:2, and the primer is SEQ ID NO:5.

26. The method of claim 16 wherein steps (b), (c), (d), and (e) are carried out simultaneously above room temperature during thermocycling using an enzyme that, after being exposed to a temperature of about 50°–95° C., forms the limited and longer extension products and the labeled product during steps (c) and (e).

27. The method of claim 16 wherein the label is a fluorescent label.

28. The method of claim 27 wherein the detecting the labeled product comprises fluorescence detection.

29. A method for detecting N-glycosylase activity comprising:

(a) providing an oligodeoxyribonucleotide substrate comprising (1) a 5' segment, (2) a deoxyadenosine residue comprising an adenine residue covalently bonded to a 2-deoxyribose residue through a β-linkage, or a deoxyuridine residue comprising a uracil residue covalently bonded to a 2-deoxyribose residue through a β-linkage, and (3) a 3' segment, which lies 3' to the deoxyadenosine or deoxyuridine residue, wherein the substrate is SEQ ID NO:1, SEQ ID NO:2, a mixture thereof, mixing the substrate with a sample to be tested for N-glycosylase activity to form a mixture, and incubating the mixture such that the N-glycosylase activity, if present, hydrolyzes the β-linkage, thereby releasing the adenine or uracil residue and producing an N-glycosylase product comprising an abasic site at the hydrolyzed deoxyadenosine or deoxyuridine residue and a 3' portion;

(b) inactivating the N-glycosylase activity in the mixture;

(c) treating the N-glycosylase product and any substrate that may be present in the mixture with an oligodeoxyribonucleotide primer under conditions such that a limited extension product of the primer is synthesized and, if the substrate is present in the mixture, a longer extension product of the primer is synthesized, wherein the primer is selected to be sufficiently complementary to the 3' portion of the N-glycosylase product and the substrate to hybridize therewith such that the limited extension product has a first 3' terminus corresponding to a residue to the immediate 3' side of the abasic site of the N-glycosylase product and the longer extension product has a second 3' terminus corresponding to the 5' terminus of the substrate, and wherein the primer further comprises a 5' segment thereof that does not hybridize with the N-glycosylase product or the substrate, wherein the primer is SEQ ID NO:5, wherein the limited extension product is sufficiently self-complementary to form a hairpin structure such that the first 3' terminus is base paired such that it can be further extended using the 5' segment as a template, and wherein the longer extension product is sufficiently self-complementary to form a hairpin structure, but the second 3' terminus is not base paired and cannot be extended using the 5' segment as a template;

(d) separating the limited and longer extension products from the N-glycosylase product and the substrate, respectively, on which they were synthesized to produce corresponding single-stranded molecules;

(e) treating the single-stranded molecules generated from step (d) under conditions such that additional limited and longer primer extension products are synthesized using the N-glycosylase product and any substrate that may be present as templates, and the limited primer extension products form hairpin structures and are further extended, using the 5' segment as template, such that a label is incorporated to result in a labeled product; and (f) separating and detecting the labeled product, thereby detecting N-glycosylase activity.

30. An oligodeoxyribonucleotide for use as an N-glycosylase substrate, wherein the oligodeoxyribonucleotide is SEQ ID NO:1, SEQ ID NO:2, or a mixture thereof.

31. The oligodeoxyribonucleotide of claim 30, wherein the oligodeoxyribonucleotide is SEQ ID NO:1.

32. The oligodeoxyribonucleotide of claim 30, wherein the oligodeoxyribonucleotide is SEQ ID NO:2.

33. The oligodeoxyribonucleotide of claim 30, wherein the oligodeoxyribonucleotide is a mixture of SEQ ID NO:1 and SEQ ID NO:2.

34. An oligodeoxyribonucleotide for use as a primer in an N-glycosylase assay, wherein the oligodeoxyribonucleotide is SEQ ID NO:5.

35. An oligodeoxyribonucleotide for use as a positive control in an N-glycosylase assay, wherein the oligodeoxyribonucleotide is SEQ ID NO:3, SEQ ID NO:4, or a mixture thereof.

36. The oligodeoxyribonucleotide of claim 35, wherein the oligodeoxyribonucleotide is SEQ ID NO:3.

37. The oligodeoxyribonucleotide of claim 35, wherein the oligodeoxyribonucleotide is SEQ ID NO:4.

38. The oligodeoxyribonucleotide of claim 35, wherein the oligodeoxyribonucleotide is a mixture of SEQ ID NO:3 and SEQ ID NO:4.

39. A kit for detecting N-glycosylase activity comprising an N-glycosylase substrate oligodeoxyribonucleotide, wherein the substrate oligodeoxyribonucleotide is SEQ ID NO:1, SEQ ID NO:2, or mixtures thereof; a positive control oligodeoxyribonucleotide, wherein the positive control oligodeoxyribonucleotide is SEQ ID NO:3, SEQ ID NO:4 or mixtures thereof; a primer oligodeoxyribonucleotide, wherein the primer oligodeoxyribonucleotide is SEQ ID NO:5; and a container in which the substrate, positive control, and primer oligodeoxyribonucleotides are disposed.

* * * * *